United States Patent
Guillamaud

(10) Patent No.: US 12,427,225 B2
(45) Date of Patent: Sep. 30, 2025

(54) ELASTOMER COMPOSITION

(71) Applicant: URGO RECHERCHE INNOVATION ET DEVELOPPEMENT, Chenove (FR)

(72) Inventor: Christelle Marie Aline Guillamaud, Chenove (FR)

(73) Assignee: URGO RECHERCHE INNOVATION ET DEVELOPPEMENT, Chenove (FR)

( * ) Notice: Subject to any disclaimer, the term of this patent is extended or adjusted under 35 U.S.C. 154(b) by 913 days.

(21) Appl. No.: 17/632,267

(22) PCT Filed: Jul. 29, 2020

(86) PCT No.: PCT/FR2020/051395
§ 371 (c)(1),
(2) Date: Feb. 2, 2022

(87) PCT Pub. No.: WO2021/023926
PCT Pub. Date: Feb. 11, 2021

(65) Prior Publication Data
US 2022/0280685 A1  Sep. 8, 2022

(30) Foreign Application Priority Data
Aug. 2, 2019 (FR) .................................... 1908880

(51) Int. Cl.
*A61L 26/00* (2006.01)

(52) U.S. Cl.
CPC ....... *A61L 26/0052* (2013.01); *A61L 26/0066* (2013.01); *A61L 26/0071* (2013.01); *A61L 26/0085* (2013.01)

(58) Field of Classification Search
CPC .................................................. A61L 26/0052
See application file for complete search history.

(56) References Cited

U.S. PATENT DOCUMENTS

| 6,080,797 A | 6/2000 | Nishida |
| 6,270,794 B1 | 8/2001 | Cilento et al. |
| 2018/0221534 A1* | 8/2018 | Burlot ............... C09J 123/0853 |

FOREIGN PATENT DOCUMENTS

| EP | 0130061 A1 | 1/1985 |
| EP | 3357517 A1 | 8/2018 |

OTHER PUBLICATIONS

International Search Report (with English Translation) and Written Opinion (Machine Translation) issued on Nov. 20, 2020 in corresponding International Patent Application No. PCT/FR2020/051395; 15 pages.

* cited by examiner

*Primary Examiner* — Michael B. Pallay
(74) *Attorney, Agent, or Firm* — Maier & Maier, PLLC

(57) ABSTRACT

A composition based on triblock copolymers of the ABA type, including two styrene thermoplastic terminal blocks A, glassy at use temperature, and an elastomeric central block B which is a saturated olefin, at least one linear polymer of the polyisobutene type having a very low molecular weight and specific crosslinked polymer particles. The composition exhibits advantageous adhesion and holding properties on the skin which are similar to the properties obtained by matrices based on silicone elastomers. They also exhibit particularly interesting cohesion.

20 Claims, No Drawings

ELASTOMER COMPOSITION

FIELD

The present invention relates to a novel composition based on triblock copolymers of the ABA type, comprising two styrene thermoplastic terminal blocks A, glassy at use temperature, and an elastomeric central block B which is a saturated olefin, at least one linear polymer of the polyisobutene type having a very low molecular weight and specific crosslinked polymer particles. The present composition exhibits advantageous adhesion and holding properties on the skin which are similar to the properties obtained by means of matrices based on silicone elastomers. They also exhibit particularly interesting cohesion.

The present invention also relates to a dressing comprising a matrix obtained from such an elastomeric composition.

BACKGROUND

Silicone elastomers are widely known compounds. They indeed have exceptional physical and mechanical properties and are used in many fields (automotive, medical devices, childcare, optics, cosmetics, etc.). In the field of adhesives, silicone elastomers are particularly advantageous, in particular in their application to the skin, wounds, skin appendages or mucous membranes. They are "soft" adhesives, which are not aggressive for the skin in the sense that they are well tolerated, while having good adhesion resistance over time. They are also repositionable, atraumatic during their removal and therefore well tolerated by the skin, in particular fragile skins such as peri-lesional skin. These adhesives can be applied, removed and reapplied without leaving residue or causing redness. However, the manufacturing processes for silicone elastomers are quite complex: whether they are obtained by hot or cold vulcanization, their manufacturing process must comply with very precise temperature and humidity conditions. By the nature of the components entering into their composition and their obtention process, silicone elastomers are therefore expensive.

Additionally, when intended for medical use, silicone elastomers must be sterilized. However, these compounds can only be sterilized by a very specific method with ethylene oxide, because their exposure to any light radiation (constituting a conventional sterilization technique) causes a modification in their structure, resulting in their adhesive properties being degraded.

SUMMARY

Thus, the present invention proposes to develop a specific composition based on non-silicone elastomers exhibiting interesting adhesion and holding properties on the skin, being close to the properties obtained by means of compositions based on silicone elastomers. Such compositions, exhibiting the desired adhesion properties, can in particular be obtained without adding tackifying resin. In fact, in order to impart sufficient tack properties to the compositions based on non-silicone elastomers, it is generally required to introduce a tackifying resin. The presence of such a resin imparts, to the touch, a drier and therefore less soft and more aggressive tack resulting in poorer conformability and very high adhesion. Adding a resin can, moreover, cause the whole composition to be unstable.

More precisely, it has been discovered, and this constitutes the basis of the present invention, that compositions employing at least one specific triblock elastomeric copolymer, of the styrene—saturated olefin—styrene type, at least one polymer of the polyisobutene type having a very low molecular weight, and particles of a specific crosslinked polymer, in a predetermined amount by weight, make it possible to produce elastomeric matrices exhibiting improved adhesive properties, similar to those obtained with silicone elastomers, while exhibiting improved cohesion.

The invention thus also covers an elastomeric matrix obtained by means of a composition as described above.

The elastomeric matrices of the invention can be obtained from a conventional manufacturing process. They can be sterilized by radiation unlike matrices using silicone adhesives.

Once applied, the obtained elastomeric matrices, which can be implemented in various devices, in particular adhesives, such as for example dressings, are easy to handle and are resistant, they are repositionable, allow painless removal when applied onto the skin, mucous membranes or skin appendages, and exhibit satisfactory holding over time.

Thus according to a first aspect, the present invention relates to a composition comprising:
- 2.5 to 20% of a styrene—saturated olefin—styrene triblock copolymer
- 30 to 96.5% by weight of a polyisobutene with a number molecular weight of between 700 g·mol$^{-1}$ and 3000 g·mol$^{-1}$, and
- 1 to 25% by weight of particles of a crosslinked polymer having a carboxylate group density of between 2.0 and 12.0 meq/g and an average pore size of between 0.005 and 1.0 µm, the percentages being expressed by weight, relative to the total weight of the composition.

According to a second aspect, the present invention relates to a composition comprising:
- 4 to 12% by weight of a styrene—saturated olefin—styrene triblock copolymer,
- 30 to 70% by weight of a polyisobutene with a number molecular weight of between 700 g·mol$^{-1}$ and 3000 g·mol$^{-1}$,
- 20 to 70% by weight of a plasticizer, and
- 1 to 25% by weight of particles of a crosslinked polymer having a carboxylate group density of between 2.0 and 12.0 meq/g and an average pore size of between 0.005 and 1.0 µm, the percentages being expressed by weight, relative to the total weight of the composition.

In particular, according to a preferred embodiment of the first and second aspects of the invention, the composition further comprises 0.05 to 0.4% by weight of an antioxidant, the percentages being expressed by weight, relative to the total weight of the composition. The antioxidant agent makes it possible to have a stable composition over time.

According to a third aspect, the present invention relates to an elastomeric matrix obtained from such a composition and a dressing comprising said elastomeric matrix.

Finally, a further object of the invention is the use of particles of a crosslinked polymer having a carboxylate group density between 2.0 and 12.0 meq/g and an average pore size between 0.005 and 1.0 µm to improve the cohesion of an elastomeric matrix as previously described.

DETAILED DESCRIPTION

Styrene—Saturated Olefin—Styrene Triblock Copolymer

The composition according to the invention comprises at least one triblock block copolymer of the ABA type (styrene—saturated olefin—styrene).

The block copolymers used in the context of the invention are triblock copolymers of the ABA type comprising two styrene end blocks A (non-elastomeric blocks, glassy at use temperature, in particular thermoplastic) and a saturated olefin central block B (elastomeric block). They are in particular prepared by anionic or radical polymerization techniques. The triblock copolymers can assume various structures: linear, star-shaped (also called radial), branched or even comb-shaped.

For the sake of simplicity, in the present description, the polymeric blocks constituting the abovementioned copolymers are designated by the nature of their recurring units. Thus, the expression "block" or "styrene A block" denotes a poly(styrene) block and the expression "block" or "saturated olefin block" denotes a poly(saturated olefin) block.

The blocks A are therefore non-elastomeric styrenic (or polystyrenic) blocks.

The blocks B of saturated olefins can for example be:
hydrogenated polyethylene followed by a hydrogenated polybutylene block: the block copolymer then has the structure: polystyrene-poly(ethylene-butylene)-polystyrene and bears the name: SEBS;
hydrogenated polyethylene followed by a hydrogenated polypropylene block: the block copolymer then has the structure: polystyrene-poly(ethylene-propylene)-polystyrene and bears the name: SEPS;
hydrogenated polyethylene followed by a hydrogenated polyethylene block then by a hydrogenated polypropylene block: the block copolymer then has the structure: polystyrene-poly(ethylene-ethylene-propylene)-polystyrene and bears the name: SEEPS;
polyisoprene: the block copolymer then has the structure: polystyrene-polyisoprene-polystyrene, and bears the name: SIS;
polyisoprene followed by a polybutadiene block: the block copolymer then has the structure: polystyrene-polyisoprene-polybutadiene-polystyrene, and the name: SIBS; or
polybutadiene: the block copolymer then has the structure: polystyrene-polybutadiene-polystyrene, and bears the name: SBS.

According to a preferred embodiment, the blocks B are ethylene-butylene, ethylene-propylene or ethylene-ethylene-propylene blocks. The preferred block copolymers are thus selected from polystyrene-poly(ethylene-butylene)-polystyrene (SEBS), polystyrene-poly(ethylene-propylene)-polystyrene (SEPS) and polystyrene-poly(ethylene-ethylene-propylene)-polystyrene (SEEPS).

In the framework of the present invention, the triblock copolymers SEBS, SEPS or SEEPS having a styrene content of between 10 and 45% by weight, preferably between 10 and 35% by weight, relative to the weight of said SEBS, SEPS or SEEPS copolymer, will be preferred.

The saturated central block triblock copolymers are well known to the person skilled in the art and are, for example, marketed:
by the company KRATON under the name KRATON® G, and in particular the grades KRATON® G1651, KRATON® G1654, KRATON® G1652 or KRATON® G1650 and by the company KURARAY under the names SEPTON® and in particular the grades 8006 or 8004 for poly(styrene-ethylene-butylene-styrene) block copolymers (abbreviated SEBS);
by the company KURARAY under the name SEPTON® for poly(styrene-ethylene-propylene-styrene) block copolymers (abbreviated SEPS) and in particular grades 2005, 2006 or 2063 and for poly(styrene-ethylene-ethylene-propylene-styrene) block polymers (abbreviated SEEPS) and in particular grades 4033, 4044, 4055, 4077 or 4099;
by the company Dynasol under the name Calprène®, in particular Calprène® H6140 and H6144 for an SEBS block copolymer.

According to a preferred embodiment, the styrene—saturated olefin—styrene triblock copolymer according to the invention has a viscosity measured in a 5% (mass/mass) solution in toluene at 30° C., between 0.01 and 1 Pa·s.

Among the copolymers which have a viscosity of between 0.01 and 1 Pa·s measured in a 5% solution, mention may be made of the copolymers marketed by the company KRATON under the grades KRATON® G 1651 and KRATON® G 1654 and the copolymers marketed by the KURARAY company under SEPTON® grades 1651 or 1654.

Mention may also be made of the copolymers marketed by the company Dynasol under the grades Calprene® H 6140 and Calprene® H6144 or by the company TSRC under the grades Taipol® 6151 and Taipol® 6154 and the copolymers marketed by the company KURARAY.

According to another preferred embodiment, the styrene—saturated olefin—styrene triblock copolymer according to the invention has a viscosity measured in a 15% (mass/mass) solution in toluene at 30° C., between 0.01 and 0.5 Pa·s.

Among the copolymers which have a viscosity measured in a 15% solution of between 0.01 and 0.5 Pa·s, mention may be made of the copolymers sold by the company KRATON® under the grades KRATON® G 1650, KRATON® G 1657 and KRATON® G 1652, KRATON® G1726, and the copolymers marketed by the company KURARAY under the grades SEPTON® 8076 or 4033. Mention may also be made of the copolymers marketed by the company TSRC under the Taipol® 6150 or 6152 grades.

These viscosities are measured using a Brookfield LVI model viscometer in a solution in toluene at 5% or 15% mass/mass depending on the molecular weight of the copolymer.

Preferably, the styrene—saturated olefin—styrene triblock copolymer used in the framework of the present invention is a polystyrene-poly(ethylene-ethylene-propylene)-polystyrene (SEEPS) such as preferably Septon® 4055 or a polystyrene-poly(ethylene-butylene)-polystyrene (SEBS), such as preferably KRATON® G1654 or Calprène® H6144 and H6140.

In general, the amount of styrene—saturated olefin—styrene triblock copolymer in the composition is between 2.5 and 20% by weight, preferably between 3 and 15% by weight, preferably between 3.5 and 10%, more preferably between 4 and 8% by weight relative to the total weight of the composition.

Beside the styrene—saturated olefin—styrene triblock copolymer, the composition according to the invention can also comprise a diblock copolymer. Preferably, the diblock copolymer has the general formula AB in which A and B are as previously defined.

In the context of the invention, it is preferred to use a mixture of a triblock copolymer and of a diblock copolymer having the same blocks A and/or B, in particular because such mixtures are directly available commercially and guarantee a better miscibility of the mixture.

According to a preferred variant, the content in diblock copolymer in the mixture of styrenic triblock/diblock copolymers is of between 30 and 95% by weight, relative to the total weight of the mixture of styrenic triblock/diblock copolymers.

In particular, the mixture of diblock/triblock copolymer exhibits a controlled final level of triblocks/diblocks. Such a combination has the advantage of achieving a composition exhibiting better dissipation capacity and therefore better adhesiveness. Dissipation is the property of irreversible deformation of the adhesive layer. As it is deformed, this type of adhesive consumes energy which is dissipated in the deformation. It is this property which makes it possible in particular to have good adhesion, in the sense that a significant amount of energy is required to obtain this deformation which is not stored by the adhesive layer.

Among the mixtures of diblock/triblock copolymer known to the person skilled in the art, mention may be made, by way of example, of KRATON® G1726, the styrene content of which is 30%, or KRATON® G 1657 sold by the company KRATON, the styrene content of which is 13%.

In particular, the amount of styrene—saturated olefin diblock copolymer in the composition is between 1 and 10% by weight, preferably between 2 and 6% by weight, preferably between 2.5 and 5% by weight, relative to the total weight of the composition.

According to a particular embodiment, the styrenic triblock/diblock copolymers are present in the composition in a triblock/diblock ratio of between 1 and 3, preferably between 1.5 and 2.

Polyisobutene

Polyisobutene (PIB) is a saturated homopolymer, having a low reactivity (low oxidability), derived from the isobutylene monomer. This polyolefin has the repeat unit —[CH2-C(CH3)2]n-.

PIBs result from the cationic copolymerization of isobutylene (H2C=C(CH3)2, monounsaturated comonomer) with isoprene (H2C=C(CH3)-CH=CH2, conjugated diene). The reaction is carried out in solution in chloromethane at −95° C. in the presence of aluminum chloride (A1013). Polymer chains contain about 1 to 2% isoprene units (cis and trans). The linkage in 1,4 of the diene leaves a double bond (unsaturation).

For the purposes of the present invention, the term "very low molecular weight PIB" is understood as meaning PIB of which the number molecular weight is between 700 g·mol$^{-1}$ and 3000 g·mol$^{-1}$, preferably between 750 g·mol$^{-1}$. 1 and 1500 g·mol$^{-1}$, more preferably between 800 g·mol$^{-1}$ and 1400 g·mol−1, even more preferably between 850 g·mol$^{-1}$ and 1300 g·mol$^{-1}$, more preferably between 900 g·mol$^{-1}$ and 1200 g·mol$^{-1}$.

The number molecular weight of the PIB is measured by size exclusion chromatography according to the following method:
Solution of PIB at approximately 2 g/L in tetrahydrofuran (THF)
Injection volume: 1004
Flow rate: 1 mL/min
Detector: RI (refractive index)
Oven temperature: 35° C.+/−5° C.
RI temperature: 40° C.

The PIBs which may be used in the context of the present invention are well known to the person skilled in the art and available commercially, for example under the following trade names:
TER PIB® 950 marketed by TER France, polyisobutene having a number molecular weight of 950 g·mol$^{-1}$;
REWOPAL PIB® 1000 marketed by EVONIK, polyisobutene having a number molecular weight of 1000 g·mol$^{-1}$;
Glissopal V190 (also known under the name Safinol V190 or Safic-Chem V190, having a number molecular weight of 1000 g·mol$^{-1}$), V500 (having a number molecular weight of 1300 g·mol$^{-1}$); marketed by BASF
Dynapak® 190, Dynapak® 230 marketed by Univar, exhibiting number molecular weights of 1000 and 1050 g·mol$^{-1}$ respectively.

In the context of the present invention, the PIB is preferably contained in an amount of 45 to 97.5% of PIB by weight, relative to the total weight of the composition.

Ideally, the PIB is contained in an amount of 30 to 96.5%, preferably 30 to 65%, preferably 40 to 60%, more preferably 45 to 55% of PIB by weight, with respect to the total weight of the composition. When the amount of PIB is increased, the tack is increased, but the cohesion is decreased.

Particles of a Crosslinked Polymer

The compositions according to the present invention comprise particles of a crosslinked polymer having a carboxylate group density of between 0.005 and 1.0 meq/g and an average pore size of between 0.005 and 1.0 µm.

"Average pore size" means an average size expressed in volume, the value of which can be calculated by the formula 4 V/S where S is the specific surface area and V is the pore volume per mass unit obtained from a pore size distribution measured by the mercury compression method.

The average pore size, expressed in volume, can be determined by any process known to the person skilled in the art, for example by mercury intrusion porosimetry or nitrogen adsorption sorptometry.

For example, nitrogen adsorption sorptometry can be performed using a TriStar II Micromeritics instrument coupled to a Smart VacPrep Micromeritics. The batch to be characterized is for example subjected to a degassing phase for 24 hours at room temperature then 5 hours at 50° C. The temperature during the test is −196° C., and the pressure maintained in a range of 0<P/P$_0$<0.30 with P$_0$=saturated vapor pressure of nitrogen.

Mercury intrusion porosimetry can be performed using a powder measuring cell with a volume of 3 cm$^3$ and a capillary with a volume of 0.387 cm$^3$. The analysis is carried out in two stages: firstly, the "penetrometer-sample" set is in "low pressure" configuration (measurement of 0.52 psia (primary vacuum) up to 30 psia, i.e. 2 bars); secondly, the "penetrometer-sample" set is in "high pressure" configuration (measurement up to 60000 psia or 4000 bars). The minimum size of the accessible pores is 3 mm.

According to a preferred embodiment, the crosslinked polymer particles used in the context of the present application have a specific surface area of less than 1 m$^2$/g. The specific surface can in particular be measured by the BET method of physical adsorption, well known to the person skilled in the art.

According to a preferred embodiment, the polymer used is an organic polymer.

The polymer used has a carboxylate group density of between 2.0 and 12.0 meq/g. The carboxylate group is a polar group imparting the polymer with the desired moisture absorption properties.

There is no particular limitation as to the nature of the salt implemented for the formation of the carboxylate groups. It may for example be an alkali metal salt such as Li, Na, K, Rb and Cs, of an alkaline earth metal such as Be, Mg, Mg, Ca, Sr and Ba, other metals such as Cu, Zn, Al, Al, Mn, Ag, Fe, Co and Ni, NH4 and organic cations such as amines.

Preferably, the carboxylate salt used in the context of the present invention is sodium carboxylate.

The introduction of carboxylate groups can be carried out by any process known to the person skilled in the art. For example, a monomer carrying a carboxylate group can be homopolymerized or copolymerized with other monomers to obtain the polymer according to the invention. Alternatively, a polymer carrying carboxyl groups can be salified. Alternatively again, a polymer can first be grafted with carboxyl groups, which will then be salified. These methods for introducing carboxylate groups are described in detail in patent application U.S. Pat. No. 6,080,797.

A typical example of crosslinked polymer particles according to the invention can be produced from acrylonitrile or methacrylic acid.

In particular, the crosslinked polymer can be prepared from at least one alkyl acrylate monomer, in particular chosen from monomers of isooctyl acrylate, 2-ethylhexyl acrylate, butyl acrylate, of sec-butyl acrylate, methyl butyl acrylate, 4-methyl 2-pentyl acrylate, or vinyl acrylate.

More particularly, microparticles of a crosslinked polymer, in particular of polyacrylonitrile, according to the invention can be obtained by coagulation or by precipitation polymerization in order to provide an agglomerate of particles of polyacrylonitrile or an acrylonitrile polymer, this agglomerate or this polymer undergoes crosslinking with hydrazine or a hydrazine derivative and finally at least partial hydrolysis of the residual nitrile groups so as to achieve a carboxylate group density of between 2.0 and 12.0 meq/g. In addition, the various steps of this process make it possible to obtain an average pore size of between 0.005 and 1.0 µm.

By way of illustration, a first method allowing manufacturing of a crosslinked polymer according to the invention consists in preparing a polymer solution from an acrylonitrile polymer and a solvent, then in causing said solution to coagulate in a solvent which is not a solvent for said acrylonitrile polymer to obtain a porous acrylonitrile polymer, then crosslinking said porous polyacrylonitrile with a hydrazine, said crosslinking being finally followed by hydrolysis of the residual nitrile groups so as to obtain a carboxylate group density of between 2.0 and 12.0 meq/g and an average pore size between 0.005 and 1.0 µm.

Alternatively, a second method allowing manufacturing of a crosslinked polymer according to the invention consists in causing precipitation polymerization of a mixture of monomers containing at least 50% by weight of acrylonitrile to obtain a porous acrylonitrile polymer, then crosslinking said porous polyacrylonitrile with a hydrazine and hydrolysing the residual nitrile groups so as to obtain a carboxylate group density of between 2.0 and 12.0 meq/g and an average pore size of between 0.005 and 1.0 µm.

These methods are more precisely described in patent application U.S. Pat. No. 6,080,797.

Nevertheless, any particles having the carboxylate group density properties or of required pore size are suitable for producing a composition according to the invention. A typical variant would, for example, involve the production of such particles from methacrylic acid as disclosed in Example 5 of U.S. Pat. No. 6,080,797.

There is no particular limitation as to the shape of the polymer particles implemented according to the invention.

Within the meaning of the present invention, the crosslinked polymer according to the invention is characterized by an equilibrium relative humidity (measured at 20° C. under an atmosphere at 65% relative humidity) of between 20 and 80%, preferably between 30 and 70%.

According to a particular embodiment, the particles of crosslinked polymer according to the invention have an average size of between 0.1 and 100 µm, preferably between 0.3 and 64 µm.

According to another particular embodiment, the particles of a crosslinked polymer according to the invention have an apparent volumetric mass density of between 0.1 and 1 g/cm$^3$, preferably between 0.2 and 0.7 g/cm$^3$.

Such particles are for example marketed by the company Japan Exlan Co., Ltd under the name Taftic® HU 707E, Taftic® HU 720SF or Taftic® HU 1200P.

They can be introduced into the compositions according to the invention in powder form.

The composition according to the invention comprises 1 to 25%, preferably 2 to 20%, and more preferably 3 to 17% by weight, of a crosslinked polymer having a density of carboxylate group of between 2.0 and 12.0 meq/g and an average pore size of between 0.005 and 1.0 µm, preferably 0.03 to 15 parts by weight.

Plasticizer

According to a particular embodiment, and in particular when the method for manufacturing the elastomeric matrix is carried out via the molten route, the styrene—saturated olefin—styrene triblock copolymer, the PIB and the crosslinked polymer particles present in the composition according to the invention are associated with at least one plasticizer.

The plasticizers which may be used are well known and intended to improve the stretching, flexibility, extrudability or implementation properties of the styrene—saturated olefin—styrene triblock copolymer. For this purpose, one or several plasticizers can be used if necessary.

In general, as plasticizers, liquid compounds compatible with the central saturated olefin block of the abovementioned block copolymers will be preferred.

Among the plasticizer compounds which may be used in the compositions according to the invention, mention will in particular be made of oils, preferably mineral oils.

Alternatively, it is also possible to use synthetic products based on liquid mixtures of saturated hydrocarbons, for example the products marketed by the company TOTAL under the name GEMSEAL® and in particular the product GEMSEAL® 60 which is an isoparaffinic mixture obtained from a fully hydrogenated petroleum fraction.

In the context of the present invention, use will preferably be made of plasticizing oils and in particular mineral oils formed from paraffinic or naphthenic compounds, or from mixtures thereof, in variable proportions.

Particularly preferred plasticizing mineral oils are formed from mixtures of paraffinic and naphthenic compounds, and in particular such mixtures in which the proportion of compounds of paraffinic nature is predominant.

Among the plasticizing oils which are particularly suitable, mention may be made of the oil marketed by the company PETRO CANADA under the reference PURETOL® 9D or the BLANDOL® and RUDOL® oils marketed by Sonneborn or also the Pionier® 2076P oil or the Pionier® 7860 oil marketed by Hansen & Rosenthal.

Besides oils, the plasticizer can include petroleum jelly. The petroleum jelly used in the compositions of the invention is a petroleum jelly in compliance with the French Pharmacopoeia (in French: Pharmacopée Française) available commercially. By way of example, mention may be made of the Codex A® Vaseline marketed by Aiglon.

In the context of the present invention, the plasticizer is contained in an amount of 20 to 70%, preferably 25 to 50%, more preferably 30 to 40% by weight, relative to the total weight of the composition.

Hydrocolloids

According to an embodiment of the invention, the compositions according to the invention may comprise hydrocolloid particles.

These particles, when used in an elastomeric matrix intended to come into contact with the skin or the wound, allow painless removal and the maintaining a moist environment at the level of the wound in order to promote cicatrization.

To this end, a small amount of hydrophilic particles of a hydrocolloid is thus either deposited on the surface of the elastomeric matrix once the latter has been formed or, preferably, dispersed homogeneously within the composition according to the invention.

By "hydrocolloid" or "hydrocolloid particles" is meant herein any compound usually used by the person skilled in the art for its ability to absorb aqueous liquids such as water, physiological serum or wound exudates.

As suitable hydrocolloids, mention may be made, for example, of pectin, alginates, natural plant gums such as in particular Karaya gum, cellulose derivatives such as carboxymethylcelluloses (such as, for example, BLANOSE® 7H4XFPH marketed by Ashland) and their alkali metal salts such as with sodium or calcium, as well as synthetic polymers based on acrylic acid salts, known under the name "superabsorbents", such as for example the products marketed by the company CIBA Specialty Chemicals under the name SALCARE® SC91 as well as mixtures of these compounds.

Certain of these superabsorbents qualified as "microcolloids" because they have a particle size of less than 10 micrometers can of course also be used.

The preferred hydrocolloids in the context of the present invention are the alkali metal salts of carboxymethylcellulose, and in particular sodium carboxymethylcellulose (CMC).

The size of the hydrocolloid particles, for example measured by laser grain size, is generally between 50 and 100 µm, advantageously in the order of 80 µm.

Generally, the amount of hydrocolloid particles incorporated into the composition according to the invention will advantageously be less than or equal to 25% by weight, advantageously from 2 to 20% by weight, preferably from 5 to 18% by weight, more preferably from 10 to 15% by weight, relative to the total weight of said composition.

If the hydrocolloid particles are placed on the surface of the elastomeric matrix once the latter has been formed, their amount will preferably be in the order of 1 to 10% by weight, and more particularly of 2 to 5% by weight, relative to the total weight of said elastomeric matrix.

Antioxidants

The composition according to the invention can also comprise antioxidant agents.

The term "antioxidant agents" is herein meant to designate the compounds commonly used by the person skilled in the art to ensure the stability of the compounds entering into the formulation of the compositions, in particular with respect to oxygen, heat, ozone or ultraviolet radiation.

As examples of appropriate antioxidants, mention may in particular be made of phenolic antioxidants, such as in particular the products sold by the company BASF under the names IRGANOX® 1010, IRGANOX® 565, IRGANOX® 1076.

In general, these antioxidants can be used alone or in combination in an amount in the order of 0.05 to 1% by weight, preferably from 0.05 to 0.4% by weight, relative to the total weight of the composition.

In the context of the present invention, the use of the IRGANOX® 1010 product will be preferred in an amount of between 0.05 and 0.4% by weight, relative to the total weight of the composition.

Additional Active Ingredients

The composition according to the invention may also comprise one (or several) other active substance(s) making it possible to induce or accelerate cicatrization or which may have a favorable role in the treatment of skin or of a wound.

Among these active substances, mention may be made, in particular, by way of examples:

agents promoting cicatrization such as retinol, vitamin A, vitamin E, N-Acetyl Hydroxyproline, extracts of Centella *Asiatica*, papain, silicone, essential oils of thyme, niaouli, rosemary, sage, hyaluronic acid, the potassium octasulfate sucrose, sucralfate, allantoin, metformin;

antibacterial agents such as silver salts or complexes (such as silver sulfates, silver nitrates, silver sulfonamides or even silver-based zeolites), zinc or copper salts, metronidazole, neomycin, penicillins, clavulanic acid, tetracyclines, mynocycline, chlorotetracycline, aminoglycosides, amikacin, gentamicin, probiotics;

antiseptics such as chlorhexidine, trichlosan, biguanide, hexamidine, thymol, lugol, povidone iodine, benzalkonium and benzethonium chloride;

painkillers such as paracetamol, codeine, dextropropoxyphene, tramadol, morphine and its derivatives, corticosteroids and their derivatives;

local anesthetics such as lidocaine, benzocaine, dibucaine, pramoxine hydrochloride, bupivacaine, mepivacaine, prilocaine, etidocaine;

anti-inflammatory drugs such as non-steroidal anti-inflammatory drugs (NSAIDs), aspirin or acetylsalicylic acid, ibuprofen, ketoprofen, flurbiprofen, diclofenac, aceclophenac, ketorolac, meloxicam, piroxicam, tenoxicam, naproxen, indomethacin, naproxcinod, nimesulid, celecoxib, etoricoxib, parecoxib, rofecoxib, valdecoxib, phenylbutazone, niflumic acid, mefenamic acid.

These active agents may be used in an amount in the order of 0.01 to 20% by weight, preferably from 1 to 15% by weight, and more preferably from 2 to 10% by weight, relative to the total weight of the composition.

The presence of hydrocolloids within the composition promotes the release of those active agents.

Of course, the composition according to the invention can also comprise one or several other compounds known for their action in the debridement phase, such as for example:
enzymes;
urea.

Adjuvants

As adjuvants which can be used in the compositions according to the invention, mention may be made of compounds known to promote releasing of active agents, such as for example the Montanox® 80 or Sepinov® EMT 10 products which are commonly used in URGOTUL® products which incorporate active agents.

These adjuvants may be used in an amount in the order of 1 to 15% by weight, relative to the total weight of the composition.

According to a preferred embodiment, the composition according to the invention consists of:

2.5 to 20% of a styrene—saturated olefin—styrene tri-block copolymer 30 to 96.5% by weight of a polyisobutene with a number molecular weight of between 700 g·mol$^{-1}$ and 3000 g·mol$^{-1}$, and 1 to 25% by weight of particles of a crosslinked polymer having a carboxylate group density of between 2.0 and 12.0 meq/g and an average pore size of between 0.005 and 1.0 µm, and optionally, particles of hydrocolloid, of antioxidant, and/or of one or several active substance(s) making it possible to induce or accelerate cicatrization or which may have a favorable role in the treatment of wounds, the percentages being expressed by weight, relative to the total weight of the composition.

According to another preferred embodiment, the composition according to the invention consists of:

4 to 12% by weight of a styrene—saturated olefin—styrene triblock copolymer, 30 to 70% by weight of a polyisobutene with a number molecular weight of between 700 g·mol$^{-1}$ and 3000 g·mol$^{-1}$, 20 to 70% by weight of a plasticizer, and 1 to 25% by weight of particles of a crosslinked polymer having a carboxylate group density of between 2.0 and 12.0 meq/g and an average pore size of between 0.005 and 1.0 µm, the percentages being expressed by weight, relative to the total weight of the composition.

In particular, the compositions according to the invention are free from tackifying resins. By free from tackifying resin is meant, within the meaning of the present application, that the composition comprises less than 0.5% by weight of tackifying resin, in particular less than 0.05% by weight, and more preferably less than 0.005% by weight.

Among the tackifying resins, mention may be made of modified terpene or polyterpene resins, rosin resins, hydrocarbon resins, mixtures of cyclic, aromatic and aliphatic resins.

For example, these may be commercial products such as:
hydrogenated polycyclopentadiene resins marketed by the company ARAKAWA Chemical Industries under the name ARKON®P,
resins marketed by the company EXXON Chemical under the name ESCOREZ® and in particular the resin series 5000, which are hydrogenated,
a synthetic resin formed from C5/C9 copolymers such as that marketed by the company CRAY VALLEY under the name WINGTACK®86, or a synthetic polyterpene-based resin such as that marketed by the company CRAY VALLEY under the name WINGTACK® 10,
KRISTALEX® resins and in particular KRISTALEX® 3105SD and F100 marketed by the company EASTMAN, or Sylvares® SA100 (alpha-methylstyrene-based resin) by the company ARIZONA CHEMICAL, or
Sukorez® resins of SU-90; SU-100; SU-100S grades marketed by the company Kolon Industries.

According to a preferred embodiment, the compositions according to the invention are free from silicone elastomers. By free from silicone elastomers is meant, within the meaning of the present application, that the composition comprises less than 0.1% by weight of silicone elastomers, in particular less than 0.01% by weight, and more preferably less than 0.001% by weight.

Method for Preparing the Compositions

The compositions according to the invention can be prepared by any technique known to the person skilled in the art.

According to a preferred embodiment, the compositions according to the invention can be prepared by the "solvent" route or by the "molten" route.

By solvent route is meant, within the meaning of the present application, any method consisting in dissolving the styrene—saturated olefin—styrene triblock copolymer in a suitable solvent, said solvent being removed by evaporation at the end of the process for preparing the composition.

By "molten route" is meant any process consisting in melting the styrene—saturated olefin—styrene triblock copolymer in order to produce the mixture of the composition constituents. Preferably, the mixture is produced in a mixer or a kneader.

In the context of the present invention:

when the method for preparing the composition is carried out via the "solvent" route, the PIB is preferably present in an amount of 80 to 97.5%, preferably 80 to 95% by weight, relative to the total weight of the composition, when the method for manufacturing the matrix is carried out via the "molten" route, the PIB is preferably present in an amount of 45 to 97.5%, preferably 50 to 60%, preferably 52 to 58% of PIB by weight, relative to the total weight of the composition.

According to a preferred embodiment, when the process for preparing the composition is carried out via the "solvent" route, the composition according to the invention consists of:

2.5 to 20% of a styrene—saturated olefin—styrene triblock copolymer 30 to 96.5% by weight of a polyisobutene with a number molecular weight of between 700 g·mol$^{-1}$ and 3000 g·mol$^{-1}$, and 1 to 25% by weight of particles of a crosslinked polymer having a carboxylate group density of between 2.0 and 12.0 meq/g and an average pore size of between 0.005 and 1.0 µm, the percentages being expressed by weight, relative to the total weight of the composition.

It shall be understood that when the method for preparing the composition is carried out via the "solvent" route, the "solvent" used in the method does not belong to the composition.

According to another preferred embodiment, when the process for preparing the composition is carried out via the "molten" route, the composition according to the invention consists of:

4 to 12% by weight of a styrene—saturated olefin—styrene triblock copolymer, 30 to 70% by weight of a polyisobutene with a number molecular weight of between 700 g·mol$^{-1}$ and 3000 g·mol$^{-1}$, 20 to 70% by weight of a plasticizer, and 1 to 25% by weight of particles of a crosslinked polymer having a carboxylate group density of between 2.0 and 12.0 meq/g and an average pore size of between 0.005 and 1.0 µm, the percentages being expressed by weight, relative to the total weight of the composition.

Elastomeric Matrix:

An object of the present invention is also an elastomeric matrix obtained from a composition as described above.

In particular, the elastomeric matrix is obtained by forming a thin layer, that is to say having a thickness of 50 µm to 1 mm, preferably of 150 µm to 400 µm by calendering, or by hot casting of said composition, according to processes well known the person skilled in the art. The elastomeric matrix can be coated on a support so as to form an openwork deposit (in French: dépôt ajouré) or not. Thus, when the elastomeric matrix is intended to be applied onto the skin or onto a wound, the matrix can advantageously be coated so as to form an openwork deposit in order to achieve the desired permeability.

The elastomeric matrices obtained in the context of the present invention exhibiting improved adhesive properties, similar to those obtained with silicone elastomers.

In particular, the elastomeric matrices according to the invention exhibit a shear strength of at least 14 N, preferably of at least 15 N.

The purpose of measuring shear strength is to characterize the cohesion of the matrix, by measuring its strength when it is subjected to a linear shear phenomenon. It is carried out on elastomeric matrices obtained using a hydraulic press according to the following protocol, the operating conditions of which are detailed as an example:

The 2 plates of the hydraulic press were preheated. A silicone polyester film was deposited on the lower plate of the press (the siliconized side being disposed opposed to the lower plate). About 20 g of one of the described compositions were deposited on this face and the latter composition was covered with a non-stick plastic film, for example a siliconized—fluorinated polyester film (the siliconized—fluorinated face being placed in contact with the composition). Two 1.2 mm wedges were placed between the 2 polyester films at the ends of the lower plate of the press and the assembly was subjected to a pressure of 200 bars and to a temperature in the order of 90 to 100° C.

For the shear strength measurement, the plates thereby produced were allowed to cool down, and their thicknesses were checked with a micrometer so as to obtain a model whose composition thickness is approximately one mm, between 0.98 mm and 1.08 mm.

The elastomeric matrices according to the invention exhibit a loop tack of at least 15 cN/cm and a shear strength of at least 14 N, preferably at least 15 N.

Of course, the particular embodiments which have just been described can be implemented separately or according to any one of their combinations.

The compositions according to the invention make it possible in particular to produce elastomeric matrices exhibiting acceptable adhesiveness and painless removal when they are applied to the skin, the wound, the mucous membrane or the skin appendages.

The present invention is illustrated in the non-limiting examples presented below.

EXAMPLES

Preparation of the Compositions

The compositions of Examples 1 to 6 were prepared using the following constituents in the proportions, expressed as a percentage by weight, mentioned in Table 1 below.
Elastomer: Poly(styrene-ethylene-butylene-styrene) block copolymer (abbreviated SEBS):
  KRATON® G 1654 marketed by Kraton Polymer
  KRATON® G 1651 marketed by Kraton Polymer.
Plasticizer:
  Pionier® 2076P or Pionier® 7860 mineral oils marketed by Hansen & Rosenthal.
Antioxidant: IRGANOX® 1010 marketed by BASF.
Very Low Molecular Weight PIB:
  Safinol® V190 or Safi-Chem® V190 (new trade name for Safinol® V190), marketed by SAFIC, having a molecular weight Mn of 1000 g·mol$^{-1}$.

Crosslinked Polymer Particles:
Taftic® HU-720 SF from the company Japan Exlan Co., Ltd.

Manufacture of the composition via the molten route:
In a vertical mixer, the plasticizer and the PIB were successively introduced at a set temperature of 80° C. and stirred until a homogeneous mixture was obtained, then the particles of a crosslinked polymer were added.

The copolymer(s) and the antioxidant were then introduced while stirring, then the set temperature was brought to 150° C. and stirring was performed until a homogeneous mixture was obtained.

It was then allowed to cool, then the mixer was emptied.

Subsequently, elastomeric matrices were produced from the compositions to be tested, by applying high pressure using a hydraulic press according to the following protocol:
The 2 plates of the hydraulic press were preheated to 90° C. On the lower plate of the press a polyurethane (PU) film and a polypropylene non-woven were deposited (the polypropylene non-woven face being disposed opposed to the lower plate, the PU face being covered with a paper liner). About 3,5 g of one of the described compositions were deposited on this face and the latter composition was covered with a siliconized polyester film (the siliconized side being placed in contact with the composition). Two 0.25 mm wedges were placed between the 2 polyester films at the ends of the lower plate of the press and the assembly was subjected to a pressure of 200 bars and to a temperature in the order of 90 to 100° C.

The matrices produced thereby were allowed to cool, the paper liner located on the PU film on the face opposed to the nonwoven was removed, and their thicknesses were checked with a micrometer so as to obtain a model whose thickness is in the order of 210 to 260 μm without the silicone polyester.

Shear Strength Measurement

Subsequently, polymeric matrices were produced from the compositions to be tested, by applying high pressure using a hydraulic press according to the following protocol:
The 2 plates of the hydraulic press were preheated. A silicone polyester film was deposited on the lower plate of the press (the siliconized side being disposed opposed to the lower plate). About 20 g of one of the described compositions were deposited on this face and the latter composition was covered with a non-stick plastic film, for example a siliconized—fluorinated polyester film (the siliconized—fluorinated face being placed in contact with the composition). Two 1.2 mm wedges were placed between the 2 polyester films at the ends of the lower plate of the press and the assembly was subjected to a pressure of 200 bars and to a temperature in the order of 90 to 100° C.

The plates thereby produced were allowed to cool down, and their thicknesses were checked with a micrometer so as to obtain a model whose composition thickness is approximately one mm, between 0.98 mm and 1.08 mm.

The purpose of this method is to characterize the strength of certain materials when they are subjected to a linear shear phenomenon.

Equipment, Materials, Reagents
  Dynamometer
  Plates: two rectangular stainless steel plates per test piece to be tested (possible size: 25×100×2 mm)
  Retaining material: Double-sided adhesive complex+Teslin SP600 marketed by the company PPG Teslin.
  compensation wedges: two wedges of known and identical thickness per sample to be tested (or combination of wedges making it possible to obtain twice the same thickness). Each wedge or combination must have the thickness of the sample to be tested and of the sample retaining material if applicable.

Sampling and/or Conditioning
Number of Samples≥3
Sample conditioning for at least 24 hours at 23° C.±2° C. and 50%±15% Relative Humidity.
Procedure
  Preparation of Test Pieces:
Glue the retaining material onto one end of the first metal plate so that it covers the metal plate over a length L=20 mm. Then press to properly adhere the retaining material and cut up the excess material flush with the metal plate.
Repeat the operation onto the second metal plate (length of the retaining material identical to the first plate).
Cut up a strip of the sample to be tested (1 mm thick) of width I=25 mm (width identical to that of the metal plates).
Glue the sample to be tested onto the retaining material of a metal plate, then cut up the excess of the sample strip flush with the metal plate so that the sample to be tested is indeed of length L=20 mm, and glue onto the sample the area with the retaining material of the second metal plate.
Measurement:
Mark the metal plates at the metal/sample limit
Apply a weight onto the area to be tested (20×25 mm area):
  1 kg for 15 seconds
Gently fix the device with the compensation wedges in the dynamometer jaws (pay attention to the thickness of the compensation wedges, the whole device must be laid flat so that the shear stress is indeed exerted in the vertical plane).
Test the Test Piece:
  45 seconds after removing the weight
Carry out the shear test until the test piece fails at the speed:
  v=10 mm·min$^{-1}$±0.5 mm·min$^{-1}$
Record the force/displacement curve
Check that the sample has not slipped on the plates using the previously made marks
Check that it is indeed a cohesion failure.
Expression of Results:
  The result is expressed in the form of the strength required for the test piece to fail in N (within $10^{-1}$).
  The elastomeric matrices according to the invention exhibit a shear strength of at least 14 N, preferably of at least 15 N.

TABLE 1

| Compound (%) | Example 1 | Example 2 | Example 3 | Example 4 |
|---|---|---|---|---|
| Safinol ® V190 | 55 | 52.2 | 49.5 | 46.7 |
| Kraton ® G1654 | 6 | 5.7 | 5.4 | 5.1 |
| Pionier ® 7860 | 38.8 | 36.9 | 34.9 | 33 |
| Taftic ® HU-720SF | | 5 | 10 | 15 |
| Irganox ® 1010 | 0.2 | 0.2 | 0.2 | 0.2 |
| Shear strength Failure force (N) | 13.53 | 17.12 | 21.55 | 23.40 |

The elastomeric matrices according to the invention exhibit excellent cohesion by means of a shear strength of at least 14 N, preferably at least 15 N.

The matrix obtained by means of the composition of Example 1 (comparative) does not comprise particles of Taftic® HU-720SF crosslinked polymer and has poorer shear strength, which results in poorer cohesion.

The invention claimed is:
1. A composition comprising:
  2.5 to 20% of a styrene—saturated olefin—styrene triblock copolymer
  30 to 96.5% by weight of a polyisobutene with a number molecular weight of between 700 g·mol$^{-1}$ and 3000 g·mol$^{-1}$, and
  1 to 25% by weight of particles of a crosslinked polymer having a carboxylate group density of between 2.0 and 12.0 meq/g and an average pore size of between 0.005 and 1.0 µm, the percentages being expressed by weight, relative to the total weight of the composition.
2. The composition according to claim 1, wherein the amount of styrene—saturated olefin—styrene triblock copolymer is between 3 and 15% by weight, relative to the total weight of the composition.
3. The composition according to claim 1, wherein the triblock copolymer of the styrene—saturated olefin—styrene type is a SEBS or a SEEPS.
4. The composition according to claim 1, wherein the PIB is contained in an amount of 30 to 65% of PIB by weight, relative to the total weight of the composition.
5. The composition according to claim 1, wherein the number molecular weight of the PIB is between 700 g·mol$^{-1}$ and 3000 g·mol$^{-1}$.
6. The composition according to claim 1, wherein the particles of crosslinked polymer have an average size of between 0.1 and 100 µm.
7. The composition according to claim 1, wherein the crosslinked polymer is prepared from acrylonitrile or methacrylic acid.
8. The composition according to claim 1, wherein the crosslinked polymer is prepared from at least one alkyl acrylate monomer.
9. The composition according to claim 8, wherein said at least one alkyl acrylate monomer is chosen from isooctyl acrylate, 2-ethylhexyl acrylate, butyl acrylate, sec-butyl acrylate, methyl butyl acrylate, 4-methyl 2-pentyl acrylate, and vinyl acrylate monomers.
10. An elastomeric matrix obtained from the composition according to claim 1.
11. The elastomeric matrix according to claim 10, wherein the elastomeric matrix is in the form of an openwork deposit.
12. A device comprising an elastomeric matrix according to claim 10.
13. The device according to claim 12, wherein said device is a dressing.
14. An elastomeric matrix obtained from the composition according to claim 1 comprising particles of a crosslinked polymer having a carboxylate group density between 2.0 and 12.0 meq/g and an average pore size between 0.005 and 1.0 µm to improve the cohesion of the elastomeric matrix.
15. A composition comprising:
  4 to 12% by weight of a styrene—saturated olefin—styrene triblock copolymer,
  30 to 70% by weight of a polyisobutene with a number molecular weight of between 700 g·mol$^{-1}$ and 3000 g·mol$^{-1}$,
  20 to 70% by weight of a plasticizer, and
  1 to 25% by weight of particles of a crosslinked polymer having a carboxylate group density of between 2.0 and 12.0 meq/g and an average pore size of between 0.005 and 1.0 µm, the percentages being expressed by weight, relative to the total weight of the composition.
16. The composition according to claim 15, wherein the plasticizer is contained in an amount of 20 to 70% by weight, relative to the total weight of the composition.
17. The composition according to claim 15, wherein the plasticizer is an oil.
18. The composition according to claim 17, wherein said oil is a mineral oil.

19. The composition according to claim 15, further comprising one or several active substance(s) making it possible to induce or accelerate cicatrization or which can have a favorable role in wound treatment.

20. The composition according to claim 19, comprising said one or several active substance(s) in an amount of between 0.01 and 20% by weight, relative to the total weight of the composition.

* * * * *